United States Patent [19]

Keane

[11] Patent Number: 5,040,889
[45] Date of Patent: Aug. 20, 1991

[54] SPECTROMETER WITH COMBINED VISIBLE AND ULTRAVIOLET SAMPLE ILLUMINATION

[75] Inventor: Thomas J. Keane, Sterling, Va.
[73] Assignee: Pacific Scientific Company, Anaheim, Calif.
[21] Appl. No.: 868,700
[22] Filed: May 30, 1986
[51] Int. Cl.⁵ .............................................. G01J 3/00
[52] U.S. Cl. ..................................... 356/51; 356/73; 356/328
[58] Field of Search .............. 250/461.1, 461.2, 252.1; 356/328, 334, 317, 318, 51, 73, 308, 326

[56] References Cited

U.S. PATENT DOCUMENTS

| | | | |
|---|---|---|---|
| 3,537,796 | 11/1970 | Dudeny | 356/328 |
| 3,704,953 | 12/1972 | Carter et al. | 356/326 |
| 3,805,255 | 4/1974 | Ishak | 356/186 |
| 3,910,701 | 10/1975 | Henderson et al. | 356/73 |
| 3,973,849 | 8/1976 | Jackson et al. | |
| 4,012,147 | 3/1977 | Walrafen | 356/326 |
| 4,060,327 | 11/1977 | Jacobowitz et al. | 356/328 |
| 4,100,416 | 7/1978 | Hirschfeld | 356/318 |
| 4,146,332 | 3/1979 | Moore | 356/326 |
| 4,198,849 | 4/1980 | Siess et al. | 374/1 |
| 4,205,229 | 5/1980 | Beer | 356/328 |
| 4,240,751 | 12/1980 | Linnecke et al. | 356/409 |
| 4,285,596 | 8/1981 | Landa | |
| 4,330,210 | 5/1982 | Hashimoto et al. | 356/328 |
| 4,342,516 | 8/1982 | Chamran et al. | |
| 4,407,008 | 9/1983 | Schmidt et al. | 358/93 |
| 4,509,856 | 4/1985 | Lee | 250/461.1 |
| 4,544,271 | 10/1985 | Yamamoto | 356/328 |
| 4,567,370 | 1/1986 | Falls | 250/461.1 |
| 4,583,187 | 4/1986 | Stoub | 250/252.1 |
| 4,650,336 | 3/1987 | Moll | 356/317 |
| 4,675,529 | 6/1987 | Kushida | 356/318 |
| 4,676,640 | 6/1987 | Briggs | 250/461.2 |
| 4,685,801 | 8/1987 | Minekane | 356/328 |
| 4,699,510 | 10/1987 | Algnard | 356/317 |

FOREIGN PATENT DOCUMENTS

| | | |
|---|---|---|
| 0047094 | 3/1982 | European Pat. Off. |
| 0071991 | 5/1983 | European Pat. Off. |
| 0171837 | 2/1986 | European Pat. Off. |
| 0225210 | 6/1987 | European Pat. Off. |
| 1241145 | 5/1967 | Fed. Rep. of Germany |
| 2508637 | 9/1976 | Fed. Rep. of Germany |
| 2297431 | 8/1976 | France |
| 2502783 | 10/1983 | France |
| 133363 | 12/1978 | German Democratic Rep. |
| 0049184 | 4/1979 | Japan ................................. 356/328 |
| 0153148 | 9/1983 | Japan ................................. 356/317 |
| 993063 | 5/1965 | United Kingdom |

OTHER PUBLICATIONS

"The American Heritage Dictionary", 2nd College Edition, Houghton Mifflin Company, Boston, 1982, p. 103.
Abstract, Japanese Application No. 55-22671, Akira Kawamoto.

Primary Examiner—Craig E. Church
Attorney, Agent, or Firm—Lane, Aitken & McCann

[57] ABSTRACT

In an optical instrument, a fiber optic probe is provided to irradiate a sample with visible NIR and ultraviolet light. Glass fibers carry the visible and NIR light to the probe from a visible and NIR light source and quartz fibers carry ultraviolet light to the probe from an ultraviolet source. Glass fibers carry visible and NIR light emanating from the sample to a spectrometer having a fixed grating and an array of photodetectors to receive the spectrum dispersed by the grating within the spectrometer housing. Amplifiers are also contained in the spectrometer housing severally connected to the photodetectors to amplify the output signals of the photodetectors. The probe is provided with a standard white sample pivotal into position to receive the light from the visible light source. A computer is programmed to provide automatic calibrating whenever the temperature within the housing changes more than a predetermined small amount. The automatic calibration is carried out by pivoting the white standard into position and computing calibration values from the resulting photodetector outputs. Automatic calibration is also provided when the ratio of output signals from selected ones of the photodetectors changes by more than a predetermined small percentage.

10 Claims, 6 Drawing Sheets

SPECTROMETER WITH COMBINED VISIBLE AND ULTRAVIOLET SAMPLE ILLUMINATION

This invention relates to spectrometers and more particularly to a spectrometer which is designed to facilitate the measuring of fluorescent effects in test samples.

BACKGROUND AND SUMMARY OF THE INVENTION

Fluorescent whiteners are commonly used by manufacturers to make a product brighter or whiter The fluorescent whiteners achieve the desired effect by responding to ultraviolet light and emitting visible light. There is a need to test the effect of the fluorescent whiteners, that is to determine how much additional light if any over and above the reflected visible light is emitted by the sample at different wavelengths in response to the ultraviolet radiation. One way to perform this test is to irradiate a sample with visible light, measure the resulting reflected light at different wavelengths by a spectrometer, then irradiate the sample with combined visible and ultraviolet energy, and then again measure the light given off by the sample at different wavelengths by the spectrometer.

The present invention provides an instrument which is designed to facilitate irradiating samples with visible light, near-infrared and ultraviolet energy and quickly make measurements of the resulting energy given off by the sample at different wavelengths throughout the visible and near-infrared spectrum. In accordance with the invention, a fiber optic probe is provided designed to irradiate the sample with visible, near-infrared (NIR) and ultraviolet light and to transmit visible and NIR light received back from the sample to the entrance slit of a spectrometer. The portion of the instrument for transmitting light to the sample contains glass fibers for transmitting visible and NIR light and quartz fibers for transmitting ultraviolet light. The transmitting ends of the quartz fibers and glass fibers are separated into a plurality of bundles which are distributed around an aperture in the probe to provide uniform illumination of a sample positioned over the aperture with both visible, NIR and ultraviolet light. The entrance ends of the glass fibers are arranged to receive light from a source of visible and NIR light, and the entrance ends of the quartz fibers are arranged to receive light from an ultraviolet source.

The spectrometer is provided with a fixed grating and a fixed array of photodetectors positioned to receive light dispersed into a spectrum from the fixed grating. Each photodetector of the array is positioned to detect the light from a different narrow bandwidth from the grating. The output signals of the photodetectors are amplified by amplifiers mounted within the housing of the spectrometer and the amplified signals are applied to a computer system which processes the data represented by the amplified output signals.

The probe has mounted therein a standard white sample, which is pivotable under the control of the computer system to a position in the path of the light transmitted by the fiber optics. To calibrate the instrument, the standard white sample is pivoted into position and the amplitudes of the resulting output signals from the amplifiers are stored in the computer. From these stored amplitudes, a calibration factor is computed for each photodetector and amplifier combination. This calibration factor, when multiplied by each amplified output signal would provide the same value for each photodetector if a perfect white sample were positioned over the probe aperture. These calibration factors are then used to multiply the amplified output signals from the photodetectors when a sample to be tested or measured is in position over the probe to provide the data representing the spectral energy distribution and fluorescence characteristic of the test sample.

In accordance with the invention, one or more temperature transducers are mounted in the spectrometer housing to sense the temperature within the spectrometer housing. When such a temperature transducer detects a predetermined small change in temperature in the spectrometer housing, 0.1° C. for example, the white standard sample is automatically pivoted into position and the calibration factors are recalculated. Because both the amplifiers and the photodetectors are mounted in the spectrometer housing where the temperature transducer or transducers are mounted, the automatic calibration avoids error due to temperature change for both the photodectors and the amplifiers.

In addition to automatically recalculating calibration factors whenever the temperature changes within the spectrometer housing, the computer system will also cause a recalibration to be periodically carried out at preselected time intervals.

In addition to this recalibration, the system may be operated in a mode in which at relatively short time intervals, the standard white sample is pivoted into position and the ratio of the amplified output signal from a photodetector near one end of the array to the amplified output from a photodetector near the other end of the array is determined. When this ratio changes by more than a predetermined small amount for example, 0.1 percent, the calibration factors are recalculated.

In the manufacture of the instrument, the photodetector are mounted in the spectrometer housing to be slideably movable by means of a micrometer screw in a direction to adjust the bandwidth received by each photodector. When this adjustment has been made, screws retaining the detector assembly are potted in position so that the position of the photodetectors is permanently precisely fixed in the proper position. The micrometer screw is then removed.

To use the instrument, the probe is positioned to irradiate a sample and the visible and NIR light source is energized to irradiate a sample with visible and NIR light. Measurements are then made with the array of photodetectors in the spectrometer. Next, the source of ultraviolet light is energized so that the sample is irradiated with visible, NIR and ultraviolet light and measurements are again made with the photodetectors. The difference in the results from each photodetector in the array will provide an indication of the effect of the fluorescence, if any, of the sample at the narrow bandwidth detected by the photodetector.

Because the probe is implemented by fiber optics, it can be readily applied to a large number of successive samples in rapid succession. Because the photodetectors are a fixed array, the fluorescence and reflectance from the successive samples can be measured and analyzed quickly, thus permitting measurement of samples in rapid succession.

Further advantages of the present invention will become readily apparent from the following detailed description of the invention when considered in conjunction with the drawings.

DETAILED DESCRIPTION OF A PREFERRED EMBODIMENT

Figure 1:
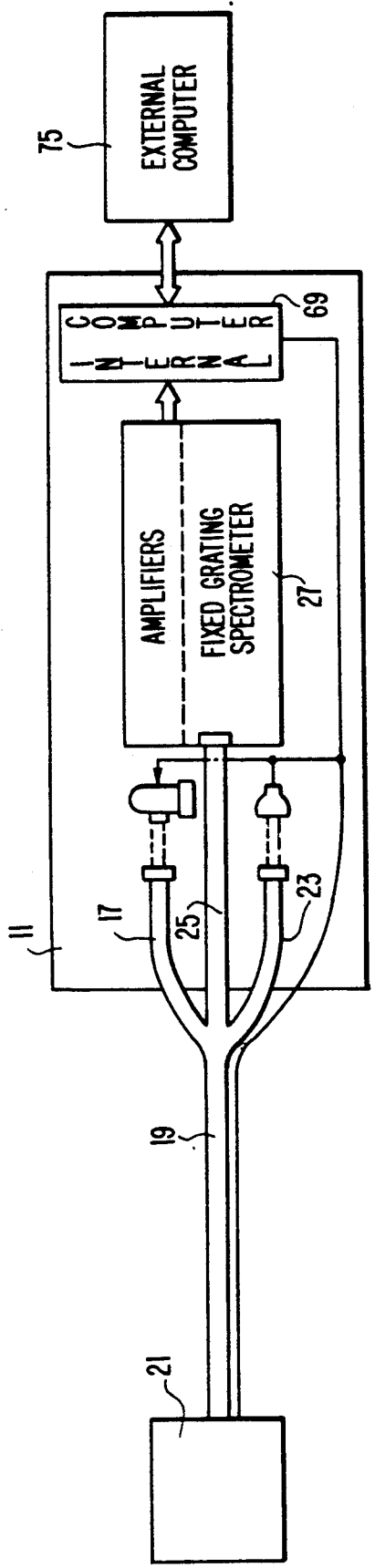
FIG. 1 is a schematic illustration of the instrument of the present invention.
Figure 2:
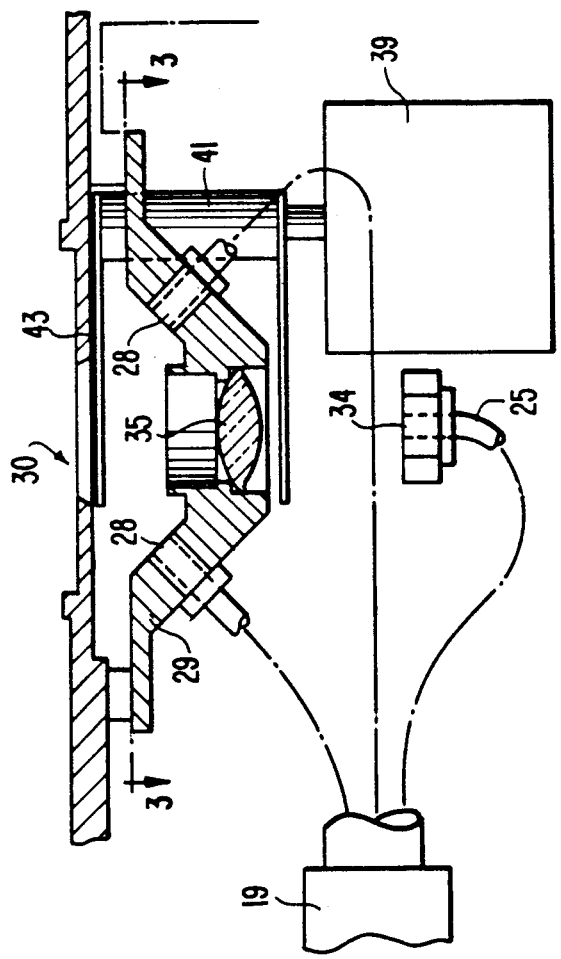
FIG. 2 is a partial sectional view illustrating the fiber optic probe of the present invention.

As shown in FIG. 1, the instrument of the present invention comprises a cabinet 11, in which a source of ultraviolet light 13 and a source of visible and NIR light 15 are mounted. The ultraviolet light 13, when energized, directs a beam of ultraviolet light on the ends of a fiber optic bundle 17 made of quartz fibers, which carry the ultraviolet light through a flexible cable 19 to a probe 21. When the source 15 is energized, it directs a beam of visible and NIR light onto the ends of a fiber optic bundle 23 made of glass fibers, which carry the light through the cable 19 to the probe 21. At the probe 21, the visible, NIR, and ultraviolet light can irradiate a sample, which diffusely reflects the visible and NIR light and, if fluorescent agents are present, fluoresces to emit light to the receiving end 34 of a fiber optic bundle 25 as shown in FIG. 2. The fiber optic bundle 25 carries the received light through the cable 19 back to the cabinet 11 and into the entrance slit of spectrometer 27 within the cabinet 11. The end of the fiber optic bundle 25, which transmits light into the spectrometer 27 is shaped into the entrance slit for the spectrometer 27 and is positioned to irradiate a fixed optical grating within the spectrometer 27.

Figure 3:
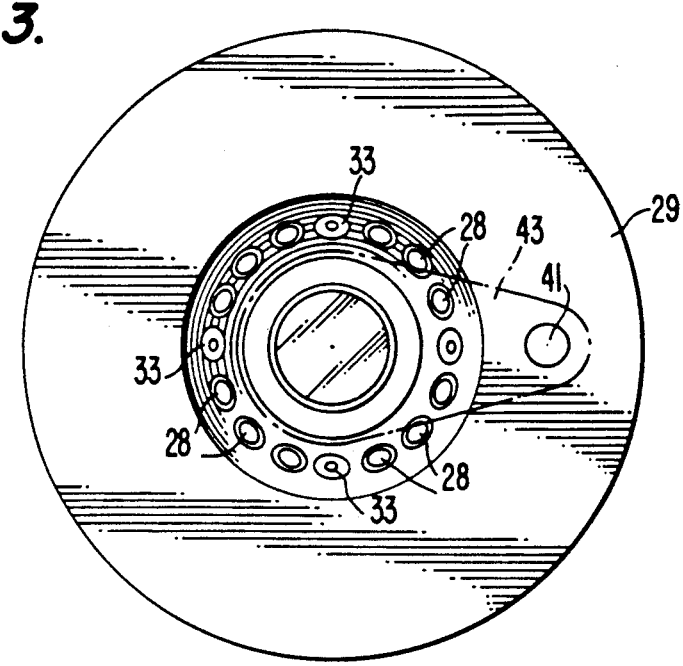
FIG. 3 is a top plan view of a fixture in the probe which mounts the transmitting ends of fiber optic bundles for transmitting light to the sample.

In the probe 21, the fiber optic bundle 23 carrying the visible and NIR light is separated into 12 round bundles 28, the ends of which are mounted in a fixture 29 and are distributed around an aperture 30 in the probe and arranged to direct light at an angle of 45 degrees on a sample positioned over the aperture 30, as shown in FIG. 2 and 3. The quartz fibers of the bundle 17 are separated into four round bundles 33 which are mounted in the fixture 29 distributed at a 90 degree intervals around the aperture 30 as shown in FIG. 3. The bundles 33 and the bundles 28 as a group, are distributed at 22½ degree intervals around the aperture 30 in the fixture 29. The bundles 33 are positioned in the fixture 29 like the bundles 28 so as to direct the ultraviolet light at an angle of 45 degrees on a sample positioned over the aperture 30. Light emanating from the sample by being diffusely reflected or emitted by fluorescence from the sample will be focused by a lens 35 onto the receiving end 34 of the fiber optic bundle 25 which carries the received light back to the spectrometer 27. The lens 35 is mounted in an aperture in the center of the fixture 29.

Figure 4:
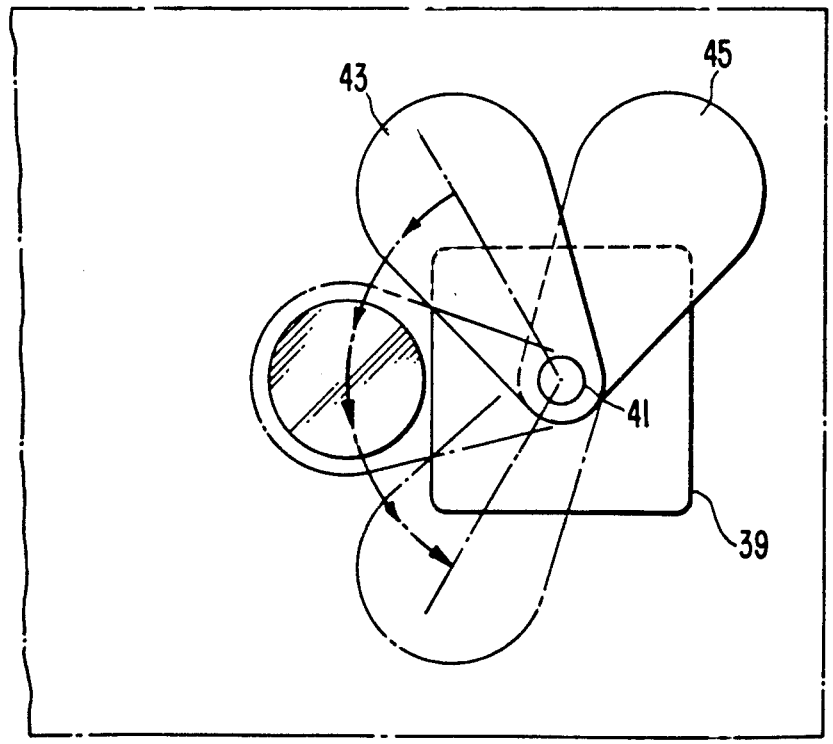
FIG. 4 is a top plan view within probe illustrating a mechanism for pivoting a standard white sample and a light blocking shutter.

Within the housing of the probe 21, is mounted a stepper motor 39, which has mounted on its output shaft 41, two paddles 43 and 45 as best shown in FIGS. 2 and 4. The paddle 43 has mounted in the end thereof, a circular white standard sample approximately the same size as the aperture 30 and the paddle 43 is pivotable by the stepper motor 39 via the shaft 41 to a position in which the white standard sample is aligned with the opening 30, just inside the opening 30 within the housing of the probe 21. When the paddle 43 is pivoted to position the white standard sample aligned with the opening 30, the visible and NIR light transmitted by the fiber optic bundle 23 and emitted from the bundle ends 28 will irradiate the white standard sample and be diffusely reflected therefrom to be received by the fiber optic bundle 25.

If the stepper motor 39 pivots the paddle 43 past the opening 30, it will bring the paddle 45 into position to block any light transmission between the lens 35 and the receiving end 34 of the fiber optic bundle 25. The paddle 45 is opaque and is used to obtain zero or null values for the spectrometer 27. The white standard sample mounted on the paddle 43 is used to obtain calibration values for the spectrometer 27.

Figure 5:
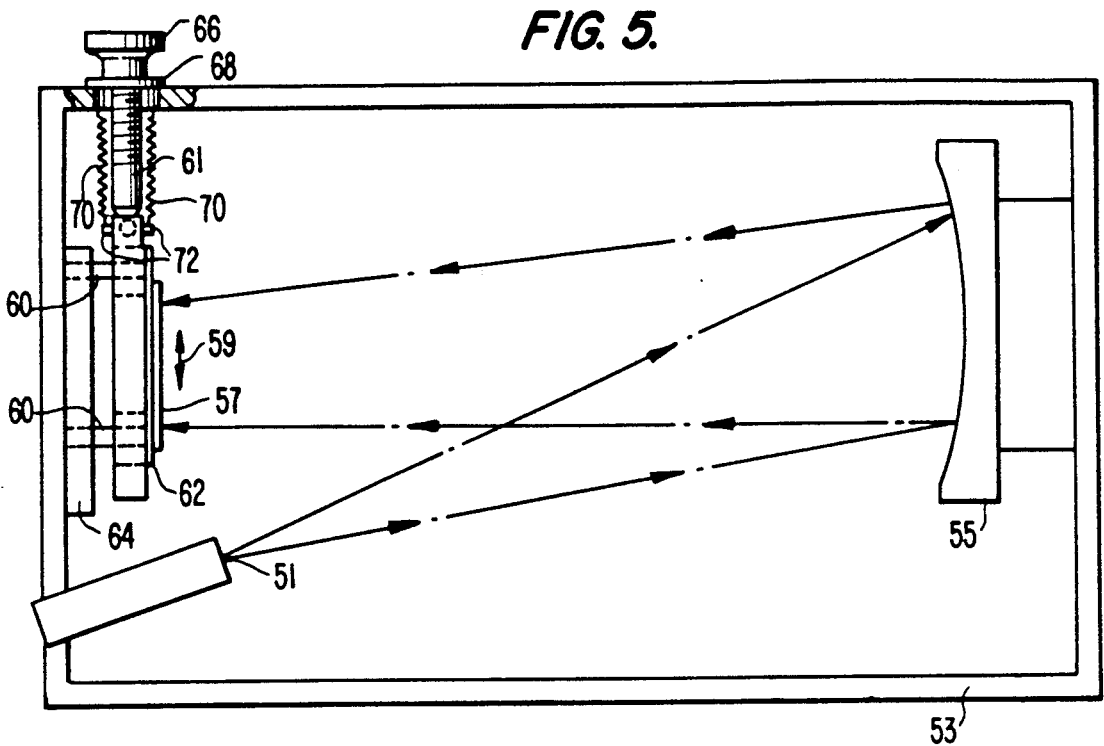
FIG. 5 is a schematic plan view within the housing of the spectrometer of the instrument illustrating the arrangement of the spectrometer components.
Figure 6:
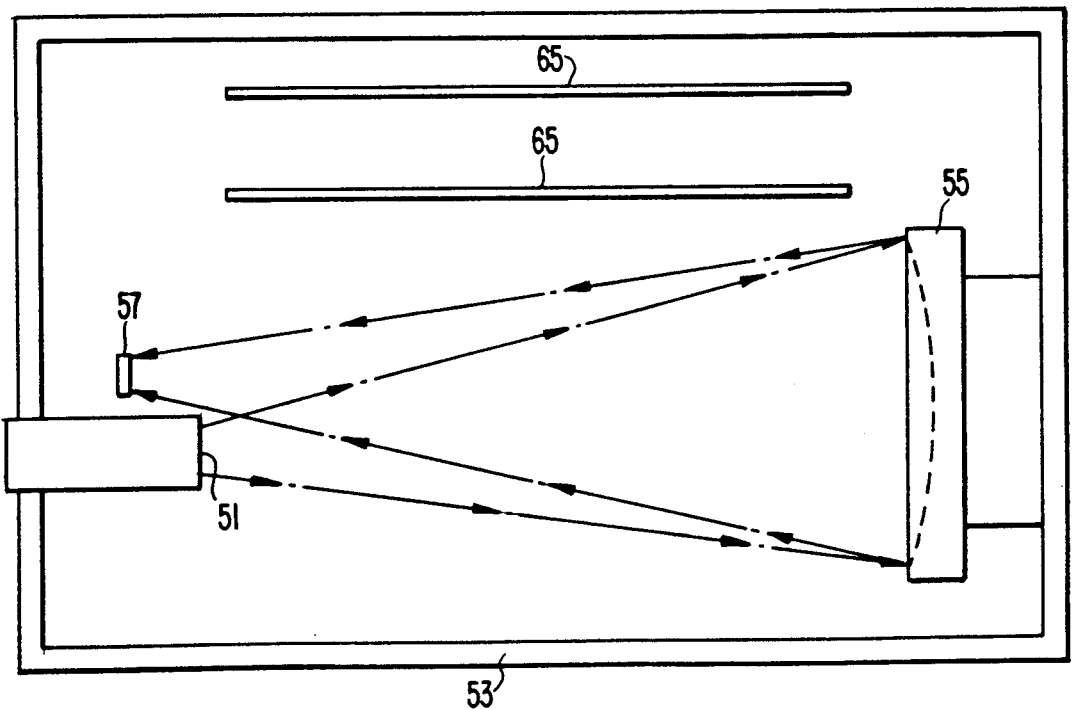
FIG. 6 is a schematic side view within the spectrometer housing illustrating the arrangement of the spectrometer components and the amplifiers for amplifying the photodetector output signals.

As shown in FIGS. 5 and 6, the light diffusely reflected or emitted by the sample and transmitted by the fiber optic bundle 25 to the spectrometer 27 is emitted from the ends of the fiber optic bundle 25 arranged in the form of an entrance slit 51 within the spectrometer housing 53 to irradiate a fixed optical reflecting grating 55. The grating 55 reflects and disperses the received light into a wavelength spectrum, which is received by a fixed array of photodetectors 57. The photodetectors are positioned relative to the spectrum at 10 nanometer wavelength intervals. In one preferred embodiment of the invention, there are 35 photodetectors positioned at 10 nanometer intervals to receive the wavelength spectrum from 380 nanometers to 720 nanometers. In another preferred embodiment, there are 70 photodetectors positioned at 10 nanometer intervals to detect the spectrum from 380 nanometers to 1070 nanometers. The individual photodetectors are essentially contiguous to one another in the array so that each photodetector detects a bandwidth of the spectrum 10 nanometers wide.

The array of photodectors 57 are mounted on a base 62, which in the manufacture of the instrument is mounted to be initially slideable with a limited degree of rectilinear movement in the direction of the arrow 59 by means of screws 60 threaded into a mounting base 64 fixed to the wall of the housing 53. Movement of the base 62 and the array of photodetectors mounted thereon is controlled by a micrometer screw 61 which is threaded into the housing 53 and the end of which is abutted against the base 62. The screw 61 is part of a micrometer having a housing 66 by which the screw 61 can be advanced into or retracted from the interior of the spectrometer. The housing 66 is positioned external to the wall of the housing 53 and has a base 68 which rests against the external surface of the wall of the housing 53. Tension springs 70 passing through small openings in the wall of the housing 53 are connected between the base 68 and posts 72 fixed to the base 62 to bias the base 62 against the end of the screw 61. The center lines of the spring 70 and the screw 61 lay in a common horizontal plane. In the manufacture of the instrument, the micrometer screw 61 is used to adjust the position of the array of photodetectors 57 so that each photodetector is properly positioned to detect the correct 10 nanometer bandwidth. After this positioning is completed, a potting compound is applied to the screws 60 holding the base 62 the screws to permanently fix the array 57 in position. Thereafter, the micrometer and the springs 70 are removed and the threaded opening for the screw 61 and the openings for the springs 70 in the housing 53 are covered by a plate.

As shown in FIG. 6, two circuit boards 65 are mounted in the housing 53 above the optical system represented by the fiber optic bundle end 51, the grating 55 and the photodetectors 57 and the light ray path therebetween. On these circuit boards 65 are amplifiers, one for each of the photodetectors of the array 57 and which are connected to amplify the output signals of the photodetectors and apply the amplified signals to an internal computer 69 mounted in the cabinet 11. Also mounted on one of these circuit boards 65 is a temperature transducer for detecting the temperature within the housing 53. The temperature transducer may be a thermistor, for example. The output signal of the temperature transducer representing the temperature within the spectrometer housing 53 is also applied to the internal computer 69.

Figure 7:
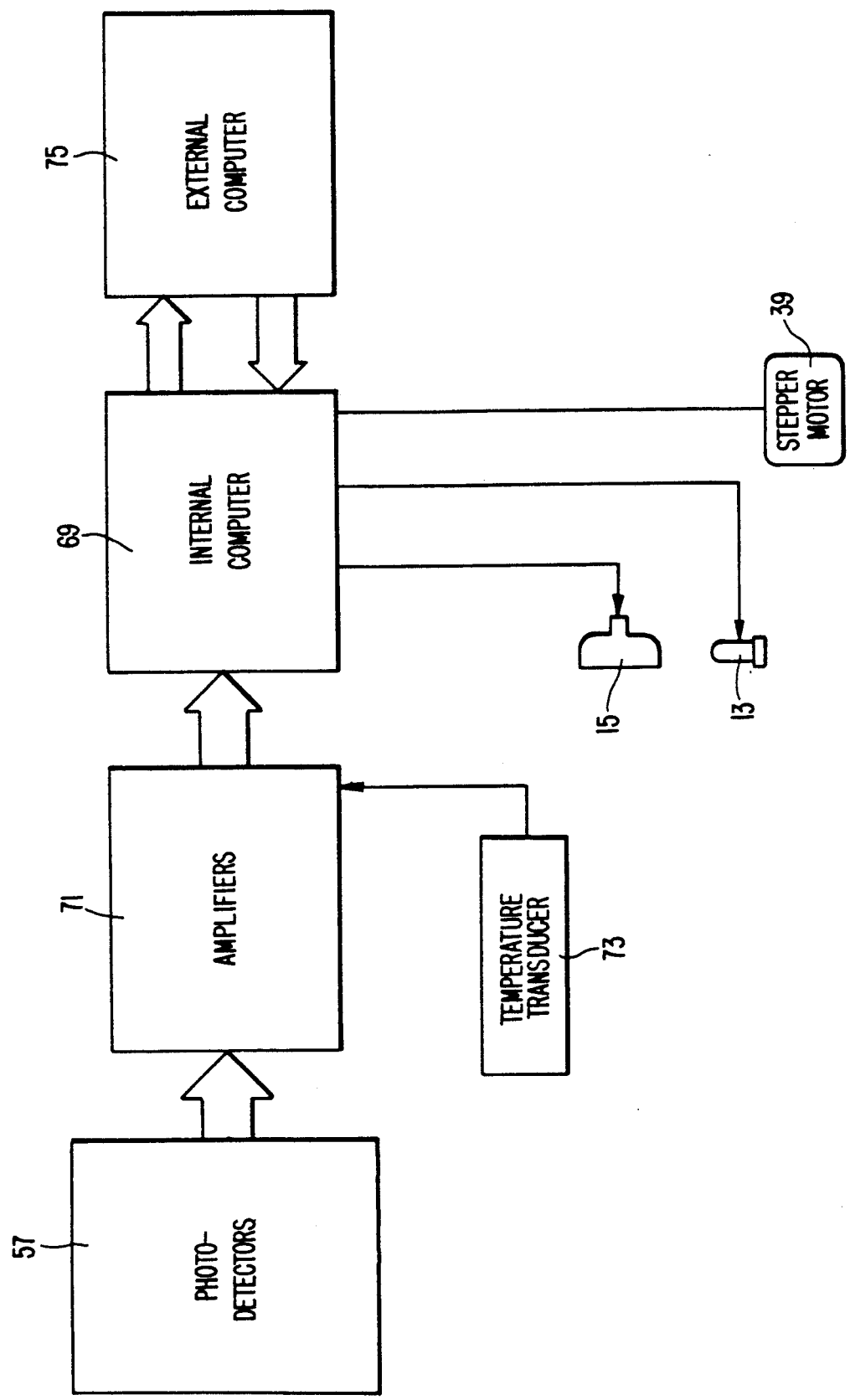
FIG. 7 is a block diagram illustrating the circuitry of the instrument.

A block diagram of the circuitry of the photodetectors, amplifiers, and internal computer 69 is shown in FIG. 7, in which the amplifiers are designated by the reference number 71 and the temperature transducer is designated by the reference number 73. As shown in FIG. 7, one of the amplifiers 71 is connected to amplify the output of signal of the temperature transducer. One of the circuit boards 65 includes a multiplexer and analog to digital converter to read the output signals of the amplifiers 71 in sequence and convert them to digital values including the amplified output signal of the temperature transducer 73. The internal computer 69 is controlled by an external computer 75 which receives commands from a user of the system and displays output data in accordance with the readings made by the instrument. The internal computer 69 is electrically connected to the ultraviolet source 13 and to the stepper motor 39 through the cable 19 and controls the energization of the UV light source as well as the stepping of the stepper motor 39. The energization of the visible and NIR source 15 is preferrably controlled by an OFF-/ON switch.

In operation, as part of an initialization process, the internal computer 69 will cause the stepper motor 39 to pivot the opaque paddle 45 into position to block light from being received by the receiving end 34 of the fiber optic bundle 25. At this time, the amplitude of the amplified output from each of the photodetectors 57 will be stored in digital form by the internal computer as a null value $N_s$ for each of the photodetectors. Then the internal computer 69 will energize the stepper motor 39 to pivot the paddle 43 to position the white standard aligned with the opening 30 of the probe 21. The amplified output values $A_s$ from each of the photodetectors are then stored in digital form. From these values $A_s$, the corresponding null values $N_s$ are subtracted to obtain a set of values $I_s = A_s - N_s$ one for each photodetector representing the diffusely reflected light intensity at each 10 nanometer bandwidth throughout the spectrum. These intensity values $I_s$ are then used to calculate calibration factors $C_\lambda$, one for each photodetector. The calibration factors are calculated by dividing the corresponding stored values of $I_s$ representing the intensities from the white sample into normalization constants $K_w$, one corresponding to each photodetector.

The resulting corresponding calibration constants $C_\lambda$ determined therefrom satisfy the equation $C = K_w/I_s$ wherein $K_w$ is the intensity value that would be obtained from a known white standard.

Figure 8:
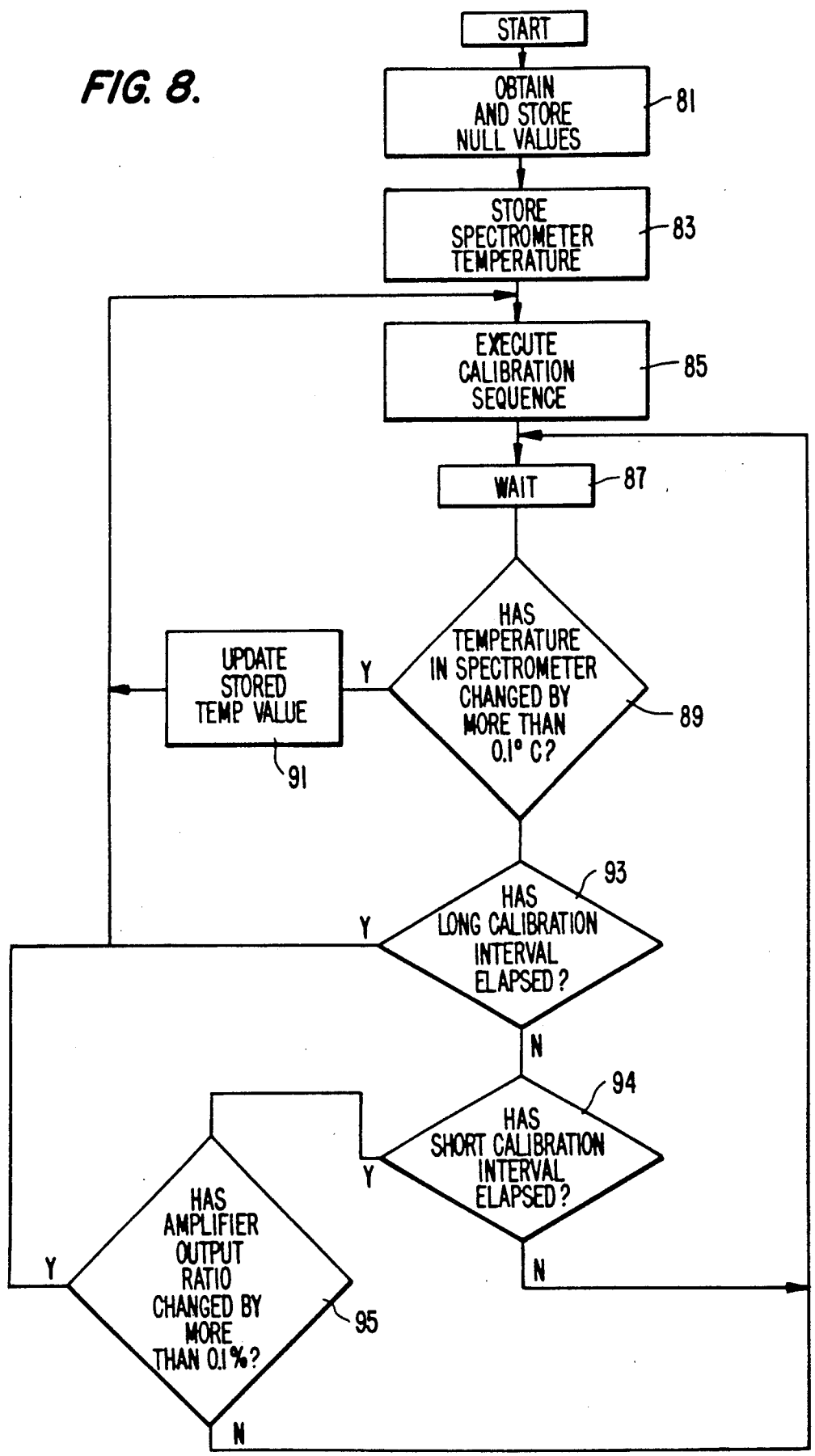
FIG. 8 is a flow chart of a program employed by the computer system to automatically carry out instrument zeroing and calibration.

FIG. 8 illustrates a flow chart of the program in the internal computer to provide for automatic recalibration of the instrument as needed. As shown in FIG. 8, when the instrument is started up, the program enters into an instruction sequence 81 in which the null values $N_s$ are obtained. To obtain the null values, the internal computer 69 pulses the stepper motor 39 to move the opaque paddle 45 into position between the lens 35 and the receiving end 34 of the fiber optic bundle 25 so as to block out light from the fiber optic bundle 25. The output value from each amplifier 71 is then read and stored in the internal computer 69 as the null value $N_s$ for that amplifier and corresponding photodetector. The program then enters instruction sequence 83 in which the output signal of the temperature transducer 73 in the spectrometer housing is read and the corresponding temperature value is stored in the memory of the internal computer 69. The program next enters instruction sequences 85 in which the calibration sequence is executed. In the calibration sequence, the internal computer sends pulses to the stepper motor 39 to pivot the paddle 43 containing the white standard into position aligned with the opening 30. The output values $A_s$ from the amplifiers 71 are then read and stored, and the null values $N_s$ are subtracted from the corresponding values $A_s$ to obtain the series of intensity values $I_s$. The $I_s$ values are then divided into the corresponding normalization constants $K_w$ to provide the calibration factors $C_\lambda$, one for each photodetector and amplifier combination. These calibration factors are stored in the memory of the internal computer 69. At the same time, the ratio of the intensity value $I_s$ obtained from one photodetector near the high end of the range to the intensity value $I_s$ obtained from another photodetector near the low end of the range is determined and this ratio is stored.

After completing the calibration sequence, the program enters into instruction sequence 87 in which the program waits for a selected interval of time which is settable by the operator by means of the external computer 75. After waiting for the selected interval, the program enters into decision sequence 89 wherein the current temperature in the spectrometer housing is read out and compared with the stored value of the temperature. If the temperature has changed by more than 0.1 degrees centigrade, the program branches into instruction sequence 91 in which the stored value of the temperature is updated in accordance with the value read out in decision sequence 89 and the program returns to instruction sequence 85 to repeat the calibration process. In this manner, each time the temperature changes by more than 0.1 degrees centigrade, the calibration constants are automatically recalculated. As a result, variations in temperature in the spectrometer housing do not cause variations in the output data obtained from the instrument.

If the temperature has not changed more than 0.1 degrees centigrade, the program proceeds into decision sequence 93, which determines whether a selected long calibration interval has elapsed. The long calibration interval is a time interval which is also selected by the operator by means of the external computer 75 and would normally be selected to be longer than the time interval of the instruction sequence 87. If the long calibration interval has elapsed, the program returns to instruction sequence 85 to repeat the calibration sequence. If the long calibration interval has not elapsed, the program enters decision sequence 94, which determines whether a short calibration interval has elapsed. The short calibration interval is also selected by the operator by means of the external computer 75 and should be substantially shorter than the long calibration interval. If the short calibration interval has not elapsed, the program returns to instruction sequence 87 and the process repeats as described above. If the short calibration interval has elapsed, the program branches to decision sequence 95. In this sequence, the internal computer 69 pulses a stepper motor to again move the paddle 43 containing the white standard into position over the probe aperture 30. At this time however, instead of reading out all of the amplifiers 71, only the amplifiers from which the ratio was determined in the calibration sequence 85 are read and the corresponding ratio from the current values is again determined. The resulting ratio is then compared with the stored value of of the ratio. If this ratio has not changed by more than 0.1 percent, the program returns to instruction sequence 87 and the process repeats as described above. However, if the ratio has changed by more than 0.1 percent, the program branches back to instruction sequence 85 to repeat the calibration sequence and the program proceeds as before. In this instance it will not be necessary to pulse the stepper motor in the calibration sequence 85 since the paddle 43 will already be in position.

In this manner, the ratio of two amplifier outputs, one selected to receive the signal from a photodetector near the upper end of the spectrum and the other selected to receive the output from a photodetector near the lower end of the spectrum is periodically computed and compared with previously stored value of this ratio and if the ratio has changed more than 0.1 percent, even if the temperature has not changed by more than 0.1 degrees centigrade, the calibration sequence will be repeated and new calibration values determined. Thus, the computer automatically updates the calibration values to compensate for drift in the sensitivity of the photodetectors or the amplifier gain characteristics, performing a recalibration after each long calibration interval and performing a recalibration after the short recalibration interval if the ratio between the output from the representative amplifiers has changed by more than 0.1 percent.

The operator by means of the external computer 75, may have the program skip decision sequences 94 and 95 and instead have the computer always proceed back to instruction sequence 87 when the long calibration interval has not elapsed. When this mode of operation is selected a shorter calibration interval would normally be selected for the decision sequence 93. The operator by means of the external computer 75 may also enter a command to cause the program to return to instruction sequence 81 to recalculate the null value, or to instruction sequence 85 to recalculate the calibration factors.

To use the instrument, a sample to be measured is placed over the probe 21 and the sample is illuminated with just the visible and NIR light. The resulting amplified output values from the samples are then read by the internal computer 69 and the null values $N_s$ are subtracted from these amplified values. The resulting differences obtained, one for each amplifier are then multiplied by the corresponding calibration constants stored in the internal computer 69 and the values obtained as a result of this multiplication will represent the reflectivity of the sample at 10 nanometer intervals. These values are fed to the external computer 75 for analysis and display. Following this operation, the computer 69 is controlled to cause the ultraviolet source 13 to be energized with the source 15 remaining energized. Light from the ultraviolet source will pass through the quartz fibers of the fiber optic bundle 17 and cause the sample to fluoresce if fluorescent agents are present and emit visible light. As a result, the sample will diffusely reflect the visible and NIR light from the light source 15 and also emit additional visible light as a result of the fluorescing of the sample in response to ultraviolet irradiation. This combined visible light emanating from the sample will be carried back to the spectrometer 27 and the internal computer 69 will obtain output values in the same manner that it did when the sample was illuminated with visible and NIR light alone. These output values are fed to the external computer 75 for analysis and display. These latter output values in comparison with values obtained when the sample was illuminated with visible and NIR light alone will provide an indication of the effect of the fluorescence of the sample. Thus, if a manufacturer has added fluorescent whiteners to the sample, the fluorescent effect of the whiteners will be determined in a convenient and efficient manner by the instrument.

Instead of having the paddle 43 pivoted into position over the opening 30, the operator by means of the external computer 75, may elect to have the paddle 43 remain in position except when a measurement is to be made. This operation minimizes the entry of dust and other harmful foreign objects into the probe 21 thus maintaining a cleaner and therefore better operating optical system. Under this scheme, the sequence for automatic calibration shown in FIG. 8 can be employed except that the paddle 43 would remain over the opening 30 and would be pivoted to unblock the opening only when a measurement is desired.

Figure 9:
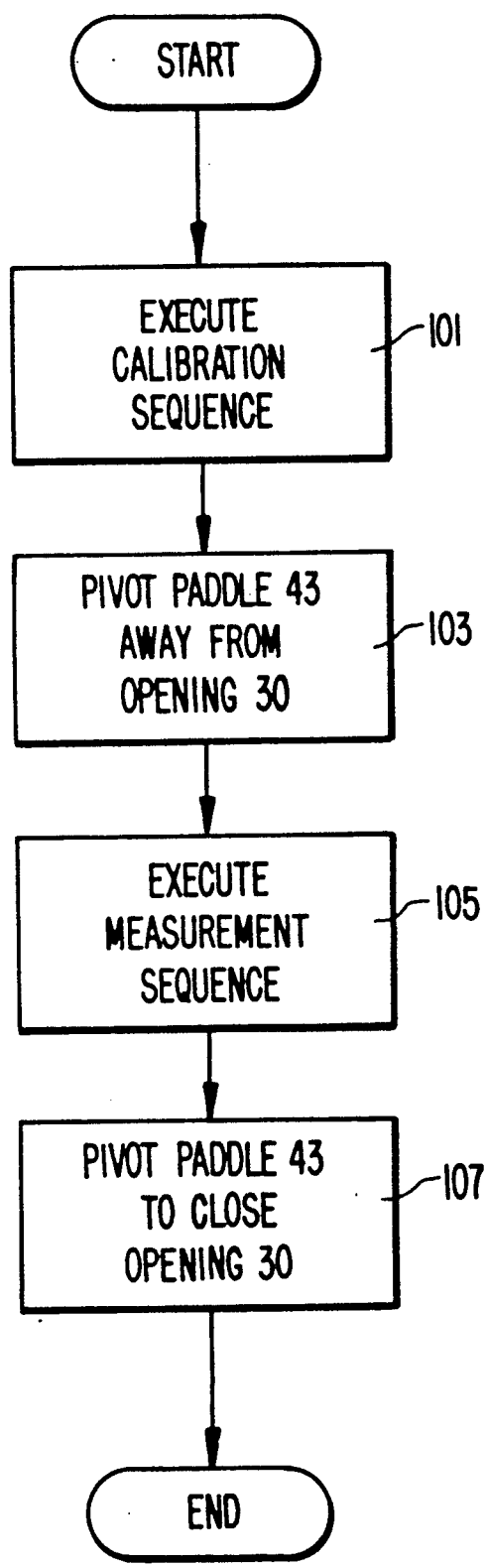
FIG. 9 is a flow chart of a program which may be employed by the computer system to take measurements on a sample in one mode of operation.

Alternatively, the calibration sequence 85 could be performed immediately before each measurement thus compensating for drift from any causes and preventing variations in the output data. The sequence of operation to make a measurement when the paddle 43 is normally retained in position over the opening 30 in the probe 21 and is moved away from the opening only when taking a measurement is illustrated by the flow chart of FIG. 9. To initiate a measurement sequence, the operator presses an appropriate key on the external computer 75. In response to the actuation of this key, the program in the internal computer 69 enters the calibration sequence 101 which is the same as calibration sequence 85 except that the paddle 43 does not have to be pivoted into position. After completion of this calibration sequence, the program enters into instruction sequence 103 in which the stepping motor pivots the paddle 43 to unblock the opening 30 and light reflected from a sample placed over the opening 30 will be directed by the lens 35 onto the entrance end 34 of the optic bundle 25. The program then enters into instruction sequence 105 in which the light emanating from the sample is measured as described above. After completion of the measurement sequence the program enters instruction sequence 107, in which the stepper motor pivots the paddle 43 back into position over the opening 30.

If desired, the internal computer 69 may be controlled to energize the ultraviolet source alone 13 so that the resulting measurement is only of the fluorescence of the sample instead of the combined reflectance and fluorescence when both the visible source 15 and the ultraviolet source are energized.

In an alternative embodiment, instead of recalculating the calibration factors each time the temperature within the housing 53 changes by a small amount, the temperature within the housing could be maintained constant by conventional temperature control system within the housing 53 or by controlling heating and or cooling in the housing 53 by the internal computer 69 in response to the temperature indicated by the temperature transducer 73. In this alternative arrangement, both the photodetectors and the amplifiers are prevented from being affected by changes in temperature since they are both mounted within the housing 53 where the temperature is controlled to be a constant value.

Many additional modifications may be made to the above described specific embodiment of the invention without departing from the spirit and scope of the invention, which is defined in the appended claims.

What is claimed is:

1. An optical instrument comprising: a source of ultraviolet light, a source of visible light, positioning means defining position to receive a test sample, a first bundle of optical fibers having transmitting ends and being capable of carrying visible light and arranged to receive visible light from said source of visible light and transmit the received visible light to said positioning means and illuminate a test sample received in said position through said transmitting ends, said transmitting ends of said first bundle being distributed in a predetermined area, a second bundle of optical fibers having transmitting ends and being operable to carry ultraviolet light and arranged to receive ultraviolet light from said source of ultraviolet light and transmit the received ultraviolet light to said positioning means and irradiate a test sample received in said position through the transmitting ends of said second bundle, the transmitting ends of said second bundle being distributed in said predetermined area among said transmitting ends of said first bundle, and means to receive visible light emanating from said test sample wherein said transmitting ends of said first bundle are arranged to illuminate said sample from different directions and said transmitting ends of said second bundle are arranged to irradiate said sample from different directions.

2. An optical instrument comprising a spectrometer including a housing defining an integral enclosed air space, a fixed grating within said housing in said air space, an array of photodetectors positioned in said housing in said air space to receive light disbursed by said grating, a plurality of amplifiers mounted in said housing in said air space and severally connected to said photodetectors to amplify the output signals of said photodetectors.

3. An optical instrument comprising a spectrometer including a fixed grating and an array of photodetectors to detect the light dispersed by said grating, a standard sample having known optical properties, means to periodically cause light emanating from said standard sample to be directed onto said grating, and means to determine whether the ratio of the output signal of a first one of said photodetectors to the output signal from a second one of said photodetectors has changed by a predetermined amount when said grating is receiving light emanating from said standard sample and if said ratio has changed by said predetermined amount to calculate a calibration factor for each of said photodetectors from the output signal produced by such photodetector when said grating is receiving light emanating from said standard sample.

4. A method of manufacturing a spectrometer having a housing, a fixed grating mounted in said housing and a fixed array of photodetectors mounted in said housing to receive light dispersed by said grating comprising the steps of mounting said array of photodetectors to be slideably movable in a linear direction within said housing to adjust the bandwidth of dispersed light received by each photodetector, extending a screw into said housing to abut against the means mounting said photodetector, adjusting the position of said photodetectors by rotating said screw to advance or retract said micrometer screw while maintaining said means mounting said photodetectors abutted against the end of said micrometer screw, thereafter potting said means mounting said photodetectors to be permanently fixed relative to said housing.

5. A method as recited in claim 4, further comprising removing said screw after permanently fixing said mounting means relative to said housing.

6. In an optical instrument for analyzing test samples including at least one photodetector, a housing containing said photodetector, means to direct light from a test sample to said photodetector, positioning means selectively operable to direct light from a standard sample to said photodetector, and means to compute a calibration factor for calibrating the output signal from said photodetector in response to the output signal of the said photodetector when said photodetector is receiving light from said standard sample, the improvement comprising:

means to detect a predetermined change in the temperature within said housing and to operate said positioning means to direct light from said standard sample onto said photodetector whenever said predetermined change in temperature occurs, said means to compute said calibration factor operating to compute said factor each time said predetermined change in temperature occurs.

7. An optical instrument as recited in claim 6, further comprising an amplifier to amplify the output signal from said photodetector, said amplifier being located within said housing, said means to calibrate the calibration factor calculating said calibration factor from the amplified output signal of said amplifier.

8. An optical instrument as recited in claim 6, wherein said instrument includes a spectrometer, said housing comprises the housing of said spectrometer, said photodetector comprises one of an array of photodetectors located within said housing, and said means to compute a calibration factor computes a calibration factor for each of said photodetectors, and means to maintain the temperature within said housing at a constant value independent of temperature variation external to said housing.

9. An instrument as recited in claim 8, further comprising a plurality of amplifiers severally connected to amplify the output signals of said photodectors, said amplifiers being mounted in said housing, said means to calculate said calibration factors calculating the calibration factors from the output signals of aid amplifiers.

10. An optical instrument comprising a source of light, a probe housing defining an opening with means to receive a test sample over said opening, means to transmit light from said source toward said opening from within said probe to irradiate a sample positioned over said opening, a standard sample normally positioned to block said opening and be irradiated by light from said source directed toward said opening from within said probe housing, and control means selectively operable to automatically move said standard sample to unblock said opening, then measure the light emanating from a sample positioned over said opening as a result of such sample being irradiated by light from said source and then to move the said standard sample back into position to block said opening, said control means being operable to measure the light emanating from said standard sample as a result of said standard sample being irradiated by light from said source.

* * * * *

UNITED STATES PATENT AND TRADEMARK OFFICE
CERTIFICATE OF CORRECTION

PATENT NO. : 5,040,889
DATED : August 20, 1991
INVENTOR(S) : Thomas J. Keane

It is certified that error appears in the above-indentified patent and that said Letters Patent is hereby corrected as shown below:

Column 1, line 13, after "whiter", insert --.--.

Column 5, line 65, "As" should be --$A_s$--.

Column 6, line 10, "Cλdetermined" should be --$C_\lambda$ determined--, and C=K$_w$/I$_s$" should be --$C_\lambda = K_w/I_s$--.

Claim 1, column 9, line 33, after "defining", insert --a--.

Claim 2, column 9, line 64, after "photodetectors", insert --, and means to maintain the temperature within said housing at a constant value independent of temperature variation external to said housing--.

Claim 9, column 11, line 1, "photodectors" should be --photodetectors--; and column 11, line 4, "aid" should be --said--.

Signed and Sealed this

Twenty-fourth Day of August, 1993

. Attest:

BRUCE LEHMAN

*Attesting Officer*   *Commissioner of Patents and Trademarks*